Figure 1:
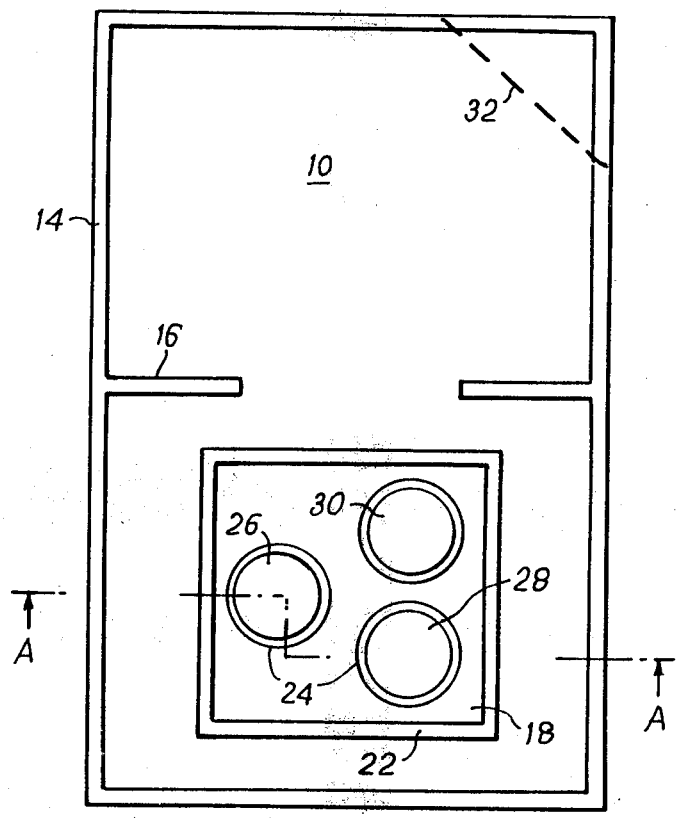

United States Patent [19]

Swaine et al.

[11] 4,200,610

[45] Apr. 29, 1980

[54] GAS-PRODUCING DEVICE

[75] Inventors: Derwent Swaine, Basingstoke, England; Henry K. Spong, Santos, Brazil; Brian M. Lewin, Basingstoke, England

[73] Assignee: Oxoid Limited, Basingstoke, England

[21] Appl. No.: 868,059

[22] Filed: Jan. 9, 1978

[30] Foreign Application Priority Data

Jan. 11, 1977 [GB] United Kingdom ............... 967/77

[51] Int. Cl.² ............................................. B01J 7/02
[52] U.S. Cl. ................................. 422/239; 435/299; 435/313; 435/801; 435/810
[58] Field of Search ................ 23/282, 281; 195/109, 195/127, 139, 142; 210/7; 422/236, 238, 164, 239, 116, 305

[56] References Cited

U.S. PATENT DOCUMENTS

| 3,246,959 | 4/1966 | Brewer | 23/282 |
| 4,038,148 | 7/1977 | Miller et al. | 23/282 X |

Primary Examiner—Michael S. Marcus
Attorney, Agent, or Firm—Wenderoth, Lind & Ponack

[57] ABSTRACT

A device for providing a non-toxic atmosphere for use in culturing anaerobic micro-organisms comprising: a closed envelope of inert material having a frangible portion which may be ruptured to allow the ingress of liquid; within the envelope a closed sachet, one part of which is formed of a gas- and liquid-permeable membrane; and material disposed within the sachet adjacent to the membrane for reacting with a liquid to generate the desired gaseous atmosphere.

7 Claims, 2 Drawing Figures

U.S. Patent

Apr. 29, 1980

4,200,610

GAS-PRODUCING DEVICE

This invention relates generally to gas-producing devices which provide a non-toxic atmosphere for culturing micro-organisms, e.g. devices which evolve gas for anaerobiosis under controlled conditions in which a predetermined volume of gas is evolved.

The growth of many micro-organisms is hindered when exposed to atmospheric conditions. Thus, a special apparatus must be supplied for their growth and provision of a non-toxic atmosphere must be introduced in the apparatus to sustain the growth of the micro-organisms. Micro-organisms such as gonococcus, meningococcus and brucella require substantially higher concentration of carbon dioxide over that of ordinary atmosphere for proper growth. Micro-organisms that are obligate anaerobes such as the bacilli of tetanus, gas gangrine, botulinus and bacteroides require the absence of oxygen for proper growth. Therefore, non-toxic atmospheres must be provided in the culturing apparatus to maintain proper growth of the desired micro-organisms.

U.S. Pat. No. 3,246,959 describes a device providing a non-toxic atmosphere for use in culturing anaerobic micro-organisms comprising: an envelope of inert material comprising a first liquid-receiving chamber and a second gas-generating chamber containing material for generating the desired gaseous atmosphere when mixed with a liquid, a wick connecting the two chambers whereby liquid passes slowly from the first chamber to the second chamber, and a passage by which the gas generated passes from the second chamber to the first chamber and so to the atmosphere. The device is actuated by rupturing the first chamber and introducing a specified volume of liquid, generally water.

Such devices have been commercially available in the United Kingdom for some years. When the device is used for generating a hydrogen/carbon dioxide atmosphere, the second chamber contains a tablet of sodium borohydride and a tablet of bicarbonate/acid. The amounts of borohydride and bicarbonate are chosen to provide enough hydrogen to react with any oxygen present and provide a reducing atmosphere to the anaerobic jar; and at least 4% by volume concentration of carbon dioxide. However, the device suffers from two main disadvantages.

Carbon dioxide is essential or stimulatory for many anaerobic organisms and it has been said that 8–10% in the atmosphere is beneficial. It has recently been shown (J. appl. Bact., 1975, 39, 167–173) that the actual carbon dioxide generated by the commercial device is variable but is much less even than 4% by volume. This apparently arises because the water reacts with the sodium borohydride with the production of hydrogen gas and sodium hydroxide solution. The bicarbonate tablet is not readily attacked by this alkaline solution; when it is attacked, much of the carbon dioxide generated dissolves and does not contribute to the desired atmosphere.

The second disadvantage of the existing device is that the water permeability of the wick is the only factor exercising control over the rate of ingress of water into the second chamber.

We have sought to avoid the first disadvantage by carrying out the reaction in such a way that the pH of the final solution is acidic, preferably below 5.0. But the reaction of water with sodium borohydride is much more violent under acidic than under alkaline conditions, so that under acid conditions it is necessary, rather than merely desirable, to exert some positive control over the rate of ingress of water into the second chamber.

The present invention provides a device for providing a non-toxic atmosphere for use in culturing anaerobic micro-organisms comprising: a closed envelope of inert material having a frangible portion which may be ruptured to allow the ingress of liquid; within the envelope a closed sachet, one part of which is formed of a gas- and liquid-permeable membrane; and material disposed within the sachet adjacent to the membrane for reacting with a liquid to generate the desired gaseous atmosphere; the surface area and permeability of the membrane being chosen to control the rate of ingress of the liquid and hence the rate of generation of the gaseous atmosphere.

The device is particularly suitable for generating a hydrogen/carbon dioxide atmosphere, but can be used in principle for generating other atmospheres, for example hydrogen or carbon dioxide or nitrogen or acetylene. For generating a hydrogen/carbon dioxide atmosphere, the material in the sachet preferably comprises sodium borohydride and a bicarbonate and a solid organic carboxylic acid in such proportions that reaction with water generates an acid solution. The chemicals for generating anaerobic atmospheres are well known in the art and will not be described here.

The envelope may be made of a flexible plastics material, or of a laminate of aluminium with a plastics material.

Preferably, the sachet takes the form of a separate generally flat package, of which one major face is of a liquid-impervious material and the other major face is the infusion membrane. The liquid-impervious material is conveniently a blister of plastics material shaped to contain one or more tablets of gas-generating material.

The device of this invention is distinguished from the prior art device of U.S. Pat. No. 3,246,959 virtue of the important fact that the membrane provides the means both of ingress of liquid into, and of egress of gas from, the sachet. This provides an automatic control of the rate of generation of gas as is more fully described below.

The membrane should be of a material that is inert to the chemicals employed and has sufficient strength not to rupture under the conditions of gas generation. Paper may be used provided it has sufficient strength. Woven or non-woven textiles may be suitable. Particularly advantageous are infusion membranes of the kind conventionally used for tea bags.

Infusion membranes are available commercially at a wide range of flow rates for both gases and liquids, e.g. from James R. Crompton and Bros. Ltd., Elton Papers Mills, Bury, Lancs. Membranes suitable for use in the present invention are likely to be those which permit a flow rate of from 100 to 1,000 cubic feet of air per square foot per minute. We prefer to use membranes which permit a flow rate of from 300 to 600, particularly 400, cubic feet of air per square foot per minute but if the membrane area were made smaller, the membrane would probably need to be thinner and vice versa. While the thickness of the membrane is obviously important, we have found that the rate of ingress of liquid into the sachet is also controlled to a considerable extent by the build-up of gas pressure therein. Thus, a first portion of liquid passes through the membrane into the sachet and reacts with material there to generate gas, which builds up pressure and helps to delay the flow of further liquid into the sachet until the gas has had an opportunity of escaping. For this reason, it is preferred that the area of the infusion membrane giving access to the interior of the sachet should be limited, and the remainder of the sachet should be formed of a liquid- and gas-impermeable material. However, the principle stated above is sufficiently definite for the same valve-like effect to be observed even if the tablets are placed in a sachet formed entirely of infusion membrane. In some circumstances, indeed, it may be advantageous to form the sheet entirely of infusion membrane.

Anaerobic jars are commerically available with a nominal size of 3 liters, and are fitted with a palladium catalyst to enable oxygen to be removed from the atmosphere by reaction with hydrogen. Suitable chemicals for generating a hydrogen/carbon dioxide atmosphere in such a jar comprise: 0.015 to 0.075 moles of sodium borohydride, or an equivalent amount of some other hydrogen-generating material; 0.01 to 0.05 moles of sodium bicarbonate, or an equivalent amount of some other carbon dioxide-generating material; and 0.01 to 0.05 moles of anhydrous tartaric acid, or an equivalent amount of some other solid organic carboxylic acid. We have found it convenient to provide these materials in the form of tablets, one containing the borohydride and the bicarbonate, and one or two more containing the organic acid. Alternatively, it would be possible to incorporate the bicarbonate with the acid.

Figure 2:
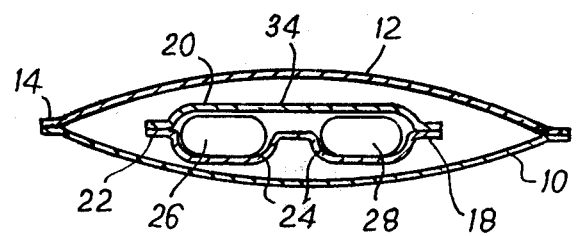

A specific device according to the present invention will now be described with reference to the accompanying drawings, in which:

FIG. 1 is a plan view of the device with the front wall of the envelope removed to show the interior; and FIG. 2 is a sectional side elevational along the line A—A of FIG. 1.

An envelope is formed of two sheets, 10, 12 of an aluminium foil/polyethylene laminate, heat-sealed together round the four edges at 14. Heat-seal lines extend inwards from the middle of the long sides of the envelope at 16, to retain a sachet in the lower half of the envelope. The sachet comprises a blister 18 of gas- and liquid-impervious pvc, and an infusion membrane 20 sealed thereto round the four edges 22 of each. The blister 18 is moulded with three circular depressions 24 to accomodate three tablets, 26, 28 and 30 which are held in position by the infusion membrane 20.

The tablets 26, 28 and 30 consititute the gas-generating material, and are formulated as follows:
Tablet 26
  Sodium borohydride—0.9 g
  Sodium bicarbonate—1.2 g
  Polyethylene glycol 6000—0.1 g
  Talc—0.1 g
Tablets 28 and 30 (each),
  Tartaric acid—2.0 g
  Disintegrator—0.1 g
  (Tartaric acid/sodium bicarbonate)
  Magnesium stearate—0.1 g The user snips the corner of the envelope at 32, places the envelope in a 3-liter anaerobic jar; pipettes 20 ml of water into the slit 32 and rapidly closes the jar. The water passes down the envelope and through the infusion membrane 20 to react with the tablets 26, 28, 30 at a controlled slow rate so as to generate hydrogen and carbon dioxide. The envelope is left in the jar for the duration of the experiment. If the jar has a nominal volume greater than 3-liters, then two or more envelopes are used.

It will be appreciated that numerous modifications may be made to this embodiment without departing from the scope of the invention. For example, better control of gas evolution may be obtained if the infusion membrane 20 is sealed to the blister 18 between, as well as around, the tablets, for example at 34 (see FIG. 2). Also, the gas-generating material can be presented differently, for example in the form of two or four or more tablets, which may be arranged in a row or a square or otherwise. Alternatively, the gas-generating material may be in granular or powder form. An advantage of having all the gas-generating material adjacent the infusion membrane is that it all reacts with the incoming water at a predictable and controllable rate.

What we claim is:

1. A hydrogen and carbon dioxide gas generating means for generating a hydrogen and carbon dioxide environment for use in culturing anaerobic microorganisms comprising a closed envelope means formed from an inert material with a frangible inlet means at one end thereof, said inlet being rupturable to afford the ingress of a liquid reactant; said envelope further having a sachet means therein forming a closed container for holding gas generating material, means in said envelope means for maintaining said sachet means in the lower half thereof, said sachet means having a wall portion thereof being formed of a gas-liquid permeable membrane adapted to permit an air flow rate therethrough of from 100 to 1000 cubic feet of air per square foot per minute; and gas generating material disposed within the sachet means adjacent to the membrane for reacting with a liquid reactant to generate the desired hydrogen and carbon dioxide atmosphere; the arrangement affording a two-way flow path transversely through the membrane, both for liquid into the sachet means and for gas from the sachet means, whereby in use the rate of ingress of liquid into the sachet means is determined in part by the surface area and permeability of the membrane and in part by the gas pressure within the sachet means.

2. A device as claimed in claim 1 wherein the sachet means takes the form of a separate flat package, of which one major face is constructed of a liquid-impervious material and the other major face is the membrane.

3. A device as claimed in claim 1 wherein the membrane is an infusion membrane.

4. A device as claimed in claim 3 wherein the infusion membrane as hereinbefore defined permits an air flow rate of from 300 to 600 cubic feet of air per square foot per minute.

5. A device as claimed in claim 1, wherein the gas generating materials are hydrogen- and carbon dioxide-generating chemicals.

6. A device as claimed in claim 5 wherein the hydrogen-generating material is sodium borohydride and the carbon dioxide-generating material is sodium bicarbonate together with a solid organic carboxylic acid, the chemicals being present in such proportions that reaction with water generates an acid solution.

7. A device as claimed in claim 6, for use in a 3-liter jar, wherein the hydrogen-generating material comprises 0.015–0.075 mols of sodium borohydride and the carbon dioxide-generating material comprises 0.01–0.05 mols of sodium bicarbonate and 0.01–0.05 mols of anhydrous tartaric acid.

* * * * *